US007718643B2

(12) United States Patent
Cho

(10) Patent No.: US 7,718,643 B2
(45) Date of Patent: May 18, 2010

(54) PHARMACEUTICAL FORMULATION

(75) Inventor: Wing-Kee Philip Cho, Princeton, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/472,021

(22) Filed: May 26, 2009

(65) Prior Publication Data

US 2009/0253675 A1  Oct. 8, 2009

Related U.S. Application Data

(60) Division of application No. 12/047,223, filed on Mar. 12, 2008, now abandoned, which is a continuation of application No. 11/716,595, filed on Mar. 12, 2007, now abandoned, which is a continuation of application No. 10/625,004, filed on Jul. 22, 2003, now Pat. No. 7,229,982.

(60) Provisional application No. 60/398,691, filed on Jul. 26, 2002.

(51) Int. Cl.
A61K 31/397 (2006.01)
A61K 31/35 (2006.01)
A61K 31/34 (2006.01)

(52) U.S. Cl. .................. 514/210.02; 514/460; 514/474

(58) Field of Classification Search ............ 514/210.02, 514/460
See application file for complete search history.

(56) References Cited

U.S. PATENT DOCUMENTS

| 4,444,784 | A | 4/1984 | Hoffman et al. |
| 4,990,535 | A | 2/1991 | Cho et al. |
| 5,100,675 | A | 3/1992 | Cho et al. |
| 5,145,684 | A | 9/1992 | Liversidge et al. |
| 5,162,117 | A | 11/1992 | Stupak et al. |
| 5,366,738 | A | 11/1994 | Rork et al. |
| 5,612,367 | A | 3/1997 | Timko et al. |
| 5,622,985 | A | 4/1997 | Olukotun et al. |
| 5,627,176 | A | 5/1997 | Kirkup et al. |
| 5,631,365 | A | 5/1997 | Rosenblum et al. |
| 5,656,624 | A | 8/1997 | Vaccaro et al. |
| 5,661,145 | A | 8/1997 | Davis |
| 5,674,893 | A | 10/1997 | Behounek et al. |
| 5,688,785 | A | 11/1997 | Vaccaro |
| 5,688,787 | A | 11/1997 | Burnett et al. |
| 5,691,375 | A | 11/1997 | Behounek et al. |
| 5,756,470 | A | 5/1998 | Yumibe et al. |
| 5,767,115 | A | 6/1998 | Rosenblum et al. |
| 5,807,834 | A | 9/1998 | Morehouse |
| 5,846,966 | A | 12/1998 | Rosenblum et al. |
| 5,976,570 | A | 11/1999 | Greaves et al. |
| 6,099,865 | A | 8/2000 | Augello et al. |
| 6,110,493 | A | 8/2000 | Guentensberger et al. |
| 6,207,822 | B1 | 3/2001 | Thiruvengadam et al. |
| 6,218,403 | B1 | 4/2001 | Daste et al. |
| 6,235,706 | B1 | 5/2001 | Gould et al. |
| 6,245,797 | B1 | 6/2001 | Winokur |
| 6,251,852 | B1 | 6/2001 | Gould et al. |
| 6,372,255 | B1 | 4/2002 | Saslawski et al. |
| RE37,721 | E | 5/2002 | Rosenblum et al. |
| 6,420,417 | B1 | 7/2002 | Keller et al. |
| 6,569,461 | B1 | 5/2003 | Tillyer et al. |
| 6,673,831 | B1 | 1/2004 | Tobert |
| 7,030,106 | B2 | 4/2006 | Cho |
| 7,229,982 | B2 * | 6/2007 | Moore et al. ............ 514/210.02 |
| 2002/0006919 | A1 | 1/2002 | Thosar et al. |

FOREIGN PATENT DOCUMENTS

| EP | 0276807 | 8/1988 |
| EP | 0457514 | 8/1996 |
| JP | 6-247854 | 9/1994 |
| JP | 85/09989 | 10/1996 |
| JP | 95/10970 | 4/1997 |
| JP | 10/501811 | 2/1998 |
| JP | 10/512592 | 2/1998 |
| JP | 2000/109882 | 4/2000 |
| JP | 2000/508659 | 7/2000 |
| JP | 2000/302672 | 10/2000 |
| JP | 2000/327589 | 11/2000 |
| JP | 2001/149042 | 6/2001 |
| WO | WO 88/05296 | 8/1988 |
| WO | WO 94/14433 | 7/1994 |
| WO | WO 95/08532 | 3/1995 |
| WO | WO 96/09827 | 4/1996 |
| WO | WO-98/01119 | 1/1998 |
| WO | WO 98/46215 | 10/1998 |
| WO | WO 99/66929 | 12/1999 |
| WO | WO 99/66930 | 12/1999 |
| WO | WO 00/32189 | 6/2000 |

(Continued)

OTHER PUBLICATIONS

Handbook of Pharmaceutical Excipients, published by American Pharmaceutical Association in 1986, pp. 78, 79, 108-110, and 234-239.
STN Registry file monograph of Registry No. 163222-31-1, "Ezetimibe", entered in data base on May 24, 1995.
Harrison's Principles of Internal Medicine, 13th Edition, vol. 1, published 1994 by McGraw-Hill, Inc. (NY), pp. 1108-1116.
Electronic online Physician's Desk Reference entry for ZOCOR® ("Description" section).
Canadian ZOCOR® Product Monograph.
SINVACOR® 20 mg package(Italian).

(Continued)

Primary Examiner—Raymond J Henley, III
(74) Attorney, Agent, or Firm—Foley & Lardner LLP

(57) ABSTRACT

The instant invention provides a pharmaceutical composition comprised of a cholesterol absorption inhibitor and an HMG-CoA reductase inhibitor, one or more anti-oxidants, microcrystalline cellulose, hydroxypropyl methylcellulose, magnesium stearate and lactose. The composition need not contain ascorbic acid in order to obtain desirable stability.

3 Claims, No Drawings

FOREIGN PATENT DOCUMENTS

| WO | WO 00/53149 | 9/2000 |
| WO | WO 00/53173 | 9/2000 |
| WO | WO 00/53566 | 9/2000 |
| WO | WO 01/08686 | 2/2001 |
| WO | WO 01/45676 | 6/2001 |
| WO | WO 01/49267 | 7/2001 |
| WO | WO 01/64221 | 9/2001 |
| WO | WO-02/20457 | 3/2002 |
| WO | WO-02/50090 | 6/2002 |
| WO | WO-02/053573 | 7/2002 |
| WO | WO 02/058696 | 8/2002 |
| WO | WO 02/058731 | 8/2002 |
| WO | WO 02/058732 | 8/2002 |
| WO | WO 02/058733 | 8/2002 |
| WO | WO 02/058734 | 8/2002 |

OTHER PUBLICATIONS

Attachment to Approval Decree for SINVACOR® 10 mg (Italian).

Gagne, C., et al., Circulation, American Hearth Association, vol. 105, No. 21, pp. 2469-2475, 2002.

Davidson, Michael, et al., Journal of the American College of Cardiology, vol. 39, No. 5, pp. 226A-227A.

Kibbe, Arthur H., Handbook of Pharmaceutical Excipeints—Third Edition, pp. 47 and 49.

Davidson, Michael, et al., Journal of the American College of Cardiology, vol. 40, No. 12, pp. 2125-2134.

Merck Frosst Canada Ltd., "Product Monograph ZOCOR®".

Communication of a Notice of Opposition dated Feb. 5, 2009, issued in European Patent Application No. 03771709.7.

Doherty, Annette M. *Annual Reports in Medicinal Chemistry*, vol. 36, Academic Press (2001), pp. 59-60.

Office Action issued Sep. 13, 2007, in U.S. Appl. No. 11/716,595, 13 pages.

Office Action issued Apr. 6, 2006, in U.S. Appl. No. 10/625,0004, 9 pages.

Office Action issued Aug. 12, 2005, in U.S. Appl. No. 10/625,0004, 12 pages.

Notice of Allowance issued Oct. 16, 2006, in U.S. Appl. No. 10/625,004, 6 pages.

* cited by examiner

PHARMACEUTICAL FORMULATION

CROSS-REFERENCE TO RELATED APPLICATIONS

The present application is a divisional of U.S. application Ser. No. 12/047,223, filed Mar. 12, 2008, now abandoned, which is a continuation of Ser. No. 11/716,595 filed Mar. 12, 2007, now abandoned, which is a continuation of U.S. application Ser. No. 10/625,004 filed Jul. 22, 2003, now U.S. Pat. No. 7,229,982, which claims the benefit of U.S. Provisional Application No. 60/398,691 filed Jul. 26, 2002, the disclosure of each of which is hereby incorporated by reference in its entirety.

The claimed invention was made by or on behalf of Merck & Co., Inc., Schering Corporation, and/or MSP Singapore LLC, who are each parties to a joint research agreement that was in effect on or before the date the claimed invention was made. The claimed invention was made as the result of activities undertaken within the scope of the joint research agreement.

BACKGROUND OF THE INVENTION

The instant invention involves a pharmaceutical formulation for bulk composition and oral dosage units comprised of the combination of a 3-hydroxy-3-methylglutaryl coenzyme A (HMG-CoA) reductase inhibitor, particularly simvastatin, with a cholesterol absorption inhibitor, particularly ezetimibe, or pharmaceutically acceptable salts, solvates or esters of these compounds, which is useful for lipid management and for preventing and treating atherosclerotic diseases and related conditions and disease events.

It has been clear for several decades that elevated blood cholesterol is a major risk factor for coronary heart disease (CHD), and many studies have shown that the risk of CHD events can be reduced by lipid-lowering therapy. Prior to 1987, the lipid-lowering armamentarium was limited essentially to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. Substantial reductions in LDL (low density lipoprotein) cholesterol accompanied by increases in HDL (high density lipoprotein) cholesterol could be achieved by the combination of a lipid-lowering diet and a bile acid sequestrant, with or without the addition of nicotinic acid. However, this therapy is not easy to administer or tolerate and was therefore often unsuccessful except in specialist lipid clinics. The fibrates produce a moderate reduction in LDL cholesterol accompanied by increased HDL cholesterol and a substantial reduction in triglycerides, and because they are well tolerated these drugs have been more widely used. Probucol produces only a small reduction in LDL cholesterol and also reduces HDL cholesterol, which, because of the strong inverse relationship between HDL cholesterol level and CHD risk, is generally considered undesirable. With the introduction of lovastatin, the first inhibitor of HMG-CoA reductase to become available for prescription in 1987, for the first time physicians were able to obtain large reductions in plasma cholesterol with very few adverse effects.

Recent studies have unequivocally demonstrated that lovastatin, simvastatin and pravastatin, all members of the HMG-CoA reductase inhibitor class, slow the progression of atherosclerotic lesions in the coronary and carotid arteries. Simvastatin and pravastatin have also been shown to reduce the risk of coronary heart disease events, and in the case of simvastatin a highly significant reduction in the risk of coronary death and total mortality has been shown by the Scandinavian Simvastatin Survival Study. This study also provided some evidence for a reduction in cerebrovascular events.

Despite the substantial reduction in the risk of coronary morbidity and mortality achieved by simvastatin, the risk is still substantial in the treated patients. For example, in the Scandinavian Simvastatin Survival Study, the 42% reduction in the risk of coronary death still left 5% of the treated patients to die of their disease over the course of this 5 year study. Further reduction of risk is clearly needed.

Certain hydroxy-substituted azetidinones such as ezetimibe (described in U.S. Pat. Nos. 5,767,115 and Re. 37721) are now known to be useful as hypocholesterolemic agents in the treatment and prevention of atherosclerosis. Cholesteryl esters are a major component of atherosclerotic lesions and the major storage form of cholesterol in arterial wall cells. Formation of cholesteryl esters is also a key step in the intestinal absorption of dietary cholesterol. Thus, inhibition of cholesteryl ester formation and reduction of serum cholesterol is likely to inhibit the progression of atherosclerotic lesion formation, decrease the accumulation of cholesteryl esters in the arterial wall, and block the intestinal absorption of dietary cholesterol.

Further risk reduction can be achieved with a combination therapy comprised of an HMG-CoA reductase inhibitor such as simvastatin with a cholesterol absorption inhibitor such as ezetimibe to provide lipid management, and to treat or reduce the risk of atherosclerotic disease; the combined use of these two active agents is described in U.S. Pat. No. 5,846,966. Since ezetimibe can be given orally once daily, like HMG-CoA reductase inhibitors such as simvastatin, it would be beneficial to combine the two active agents into a single orally administerable pharmaceutical dosage unit such as a tablet using a formulation that is stable and minimizes the degradation of the active agents.

The instant invention addresses this need by providing a novel formulation for bulk pharmaceutical composition and for oral pharmaceutical dosage units comprised of simvastatin and ezetimibe that can be produced in a robust process that provides a high quality finished product with minimal unwanted degradation by-products and desirable shelf-life stability.

SUMMARY OF THE INVENTION

The instant invention provides a novel pharmaceutical formulation comprised of a cholesterol absorption inhibitor and an HMG-CoA reductase inhibitor having desirable stability but which does not require the presence of ascorbic acid, nor does it require the presence of pre-gelatinized starch.

More particularly, the instant invention provides a pharmaceutical composition comprised of from 1% to 20% by weight of a cholesterol absorption inhibitor such as ezetimibe; from 1% to 80% by weight of an HMG-CoA reductase inhibitor such as simvastatin; and from 0.01% to 2% by weight of a stabilizing agent such as BHA. It further comprises from 1% to 80% by weight of microcrystalline cellulose; from 0.5% to 10% by weight of hydroxypropyl methylcellulose; from 0.1% to 4% by weight of magnesium stearate; and from 25% to 70% by weight of lactose. The composition may also optionally be comprised of one or more of croscarmellose sodium, citric acid, ascorbic acid and propyl gallate. Although the composition can include ascorbic acid, it is not necessary to include ascorbic acid in order to obtain desirable results. Similarly, although the composition could include pre-gelatinized starch, the composition need not include pre-gelatinized starch to obtain desirable results. The composition can be prepared in bulk form and is suitable for forming into individual oral dosage units, such as tablets, which are useful for treating vascular conditions such as hyperlipidemia including hypercholesterolemia and treating and preventing atherosclerotic disease and events such as myocardial infarction.

Another aspect of the present invention is a pharmaceutical composition comprising from 1 to 20% by weight of a cholesterol absorption inhibitor such as ezetimibe; from 1 to 80% by weight of at least one HMG-CoA reductase inhibitor; and from 0.005 to 10% by weight of at least one stabilizing agent. Additional aspects will be evident from the following detailed description.

DETAILED DESCRIPTION OF THE INVENTION

The instant invention is directed to formulations of HMG-CoA reductase inhibitors and cholesterol absorption inhibitors. More particularly the HMG-CoA reductase inhibitor is a statin, including, for example, simvastatin, lovastatin, atorvastatin, fluvastatin, pravastatin, cerivastatin, pitavastatin and rosuvastatin. The cholesterol absorption inhibitor may be selected from any of those disclosed in U.S. Pat. Nos. RE 37,721; 5,688,990; 5,656,624; 5,624,920; 5,698,548; 5,627,176; 5,633,246; 5,688,785; 5,688,787; 5,744,467; 5,756,470; 5,767,115 and U.S. patent application Ser. No. 10/166,942 filed Jun. 11, 2002, which are incorporated herein by reference. Methods of making such compounds are also disclosed in those patents. Specifically, the instant invention is directed to formulations of simvastatin and ezetimibe.

Simvastatin is marketed worldwide, and sold in the U.S. under the tradename ZOCOR®. Methods for making it are described in U.S. Pat. Nos. 4,444,784; 4,916,239; 4,820,850; among other patent and literature publications. Simvastatin is shown below as structural formula I:

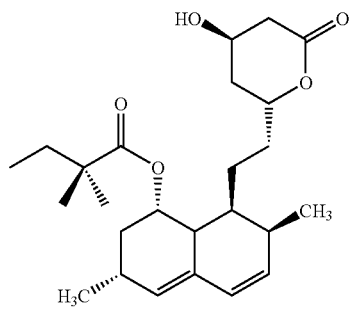

I

Ezetimibe is now marketed in the U.S. under the tradename ZETIA®. The ZETIA® formulation contains ezetimibe as the only active ingredient. Methods for making ezetimibe are described in U.S. Pat. Nos. 5,631,365; Re. 37721; 5,846,966; 5,767,115, 6,207,822; U.S. application Ser. No. 10/105,710 filed Mar. 25, 2002 and PCT No. 93/02048. Ezetimibe is shown below as structural formula II, and can be in an anhydrous or hydrated form:

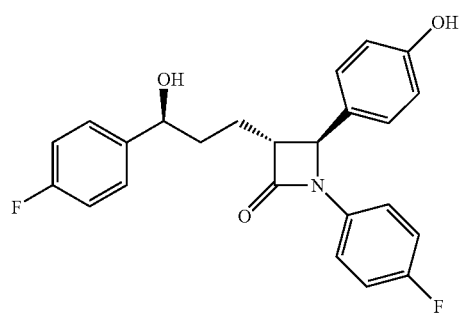

II

In addition to the HMG-CoA reductase inhibitor and cholesterol absorption inhibitor active agents, particularly simvastatin and ezetimibe, the instant oral pharmaceutical composition may contain one or more of microcrystalline cellulose, hydroxypropyl methylcellulose (HPMC), magnesium stearate, lactose and povidone (PVP). The composition is also comprised of one or more stabilizing agents including antioxidant agents such as, for example, butylated hydroxyanisole (BHA), 2,6-di-tert-butyl-4-methylphenol (BHT), propyl gallate, ascorbic acid, citric acid, edetate disodium and calcium metabisulphite, with BHA, propyl gallate and combinations thereof being preferred, and a combination of BHA with propyl gallate being most preferred. Optionally, one or more of croscarmellose sodium (CCNa), citric acid, lactic acid, malic acid, succinic acid, tartaric acid and ethylenediaminetetraacetic acid (EDTA) and salts thereof may also be included in the composition. In particular, although ascorbic acid could be included in the composition, the composition does not require the presence of ascorbic acid as a component to achieve good results. Similarly, the composition does not require the presence of pregelatinized starch as a component to achieve good results, although pregelatinized starch could be included in the composition if desired. When the term "ascorbic acid" is used herein, it is intended to include the free acid as well as salt forms thereof, such as sodium ascorbate.

It is known that ascorbic acid tends to discolor compositions, pharmaceutical and otherwise, when it is a component. When used in pharmaceutical tablets, this discoloring effect may necessitate the use of a coating over the tablet to mask the discoloration. Since the composition of this invention can be formulated without ascorbic acid, such tablets formed without ascorbic acid can be prepared without the extra step of adding a film coating. Of course, a film coating could be added if desired, for example for aesthetic purposes, but the need to add a coating to mask the discoloration caused by ascorbic acid is removed.

As used herein, the terms "pharmaceutical composition" and "composition" encompass both the bulk composition and individual oral dosage units (tablets, pills and the like) comprised of the two pharmaceutically active agents, e.g. simvastatin and ezetimibe, with the pharmaceutically inactive excipients described herein (the active agents and the excipients are collectively referred to herein as the "components" of the composition). The bulk composition is material that has not yet been formed into individual oral dosage units. The oral dosage unit form of the pharmaceutical composition is preferably a tablet.

Other than in the operating examples, or where otherwise indicated, all numbers expressing quantities of ingredients, reaction conditions, and so forth used in the specification and claims are to be understood as being modified in all instances by the term "about."

As intended herein, the total weight of a single oral dosage unit, e.g. the weight of one tablet, is determined by adding the weights of all the components (i.e., the two active agents and the excipients) in the dosage unit, and does not include the weight of any coatings which may optionally be externally applied to the dosage unit after it has been formed from the bulk composition. It also does not include any solvents used during the granulation process which are subsequently removed during drying. The total weight of a single oral dosage unit as defined above is used as the basis for calculating the weight percentage of each of the components that comprise the dosage unit. However, dosage units comprised of the components described herein that are uncoated as well as those that are coated with waxes, colorants, and the like are included within the scope of this invention.

The total weight of the bulk composition comprised of the components described herein will necessarily vary according to the amount of bulk composition that is desired to be produced. For the purpose of calculating the weight percentage of each of the components that comprise any given amount of bulk composition, the weights of all the components (i.e., the two active agents and the excipients) in a given amount of bulk composition are added together to determine the total weight of the bulk composition. As would be understood in the art, the bulk composition would not contain either solvents used in the granulation process, nor coating materials as components, and therefore such coating materials and solvents would not be included in the total weight calculation of the bulk composition.

It is understood in the art that component weight ranges and specific weight amounts used herein to describe the composition of a single oral dosage unit can be scaled proportionally to make bulk composition. Of course, the component weight percentage amounts used herein are applicable to either individual oral dosage units or to bulk composition.

Although the total weight of the pharmaceutical dosage unit can be varied as desired, for reasons of practicality it is preferable for the total weight of a single oral dosage unit to be in the range from 50 mg to 1000 mg, and particularly from 100 mg to 800 mg.

In one embodiment of this invention, the pharmaceutical composition is comprised of the cholesterol absorption inhibitor active agent, such as ezetimibe, in an amount that is from 1% to 20% by weight of the composition, and particularly from 1.25% to 10%; the HMG-CoA reductase inhibitor active agent, such as simvastatin, in an amount that is from 1% to 80% by weight of the composition, particularly from 1% to 20%, and more particularly from 5% to 10%; and at least one stabilizing agent, such as BHA, in an amount that is from 0.005% to 20% by weight, particularly from 0.01% to 2%, more particularly from 0.01% to 0.05%, and most particularly about 0.02%. In one aspect of this embodiment, the composition further comprises from 0% to 0.2% (i.e., 0.2% or less), particularly from 0.001% to 0.05%, and most particularly about 0.005% by weight of propyl gallate. As an example, an oral dosage unit having a total weight in the range from 100 mg to 800 mg may be comprised of from 1.25% to 10% by weight of ezetimibe, from 5 to 10% by weight of simvastatin, about 0.02% of BHA, and optionally about 0.005% by weight of propyl gallate.

Within this embodiment, the pharmaceutical composition, for example but not limited to an oral dosage unit having a total weight in the range from 100 mg to 800 mg, is further comprised of the percent amounts by weight of the following excipients: from 1% to 80%, particularly from 5% to 20%, and most particularly about 15% of microcrystalline cellulose; from 0.5% to 10%, particularly from 1% to 4%, and most particularly about 2% of HPMC; and from 0.1% to 4%, particularly from 0.5% to 2%, and most particularly about 1.5% of magnesium stearate.

Lactose is also a component of the composition and can be used in varying amounts to achieve the desired total tablet weight. For example, if for a single dosage unit, the combined weight of all the components other than lactose is 36.77 mg, then 63.23 mg of lactose can be added to achieve a total dosage unit weight of 100 mg. If for a single dosage unit, the combined weight of all the components other than lactose is 73.54 mg, then 126.46 mg of lactose can be added to achieve a total dosage unit weight of 200 mg. As would be understood in the art, such component weight amounts can be scaled up proportionally to make bulk composition. Generally, about 25% to 70% by weight of the composition is comprised of lactose.

In one aspect of this embodiment, croscarmellose sodium may optionally be included as a component in the composition. Accordingly, from 0% to 10% (i.e., 10% or less), particularly from 2% to 4%, and most particularly about 3% by weight of croscarmellose sodium may be included in the composition.

In another aspect of this embodiment, citric acid may optionally be included as a component in the composition. Accordingly, from 0% to 10% (i.e., 10% or less), particularly from 0.1% to 1.25%, and most particularly about 0.25% by weight of citric acid may be included in the composition.

Additionally, one or more of lactic acid, malic acid, succinic acid, tartaric acid and EDTA may optionally be included in the composition.

In a second embodiment of this invention, the pharmaceutical composition is comprised of from 1% to 20% by weight of the composition of a cholesterol absorption inhibitor, such as ezetimibe; from 1% to 80% by weight of the composition of at least one HMG-CoA reductase inhibitor, such as a statin; and at least one stabilizing agent in an amount that is from 0.005% to 10% by weight of the composition, and particularly from 0.01% to 5%, and more particularly from 0.01% to 2%.

In one aspect of this embodiment, the stabilizing agent is an antioxidant. In a further aspect, the antioxidant is selected from the group consisting of butylated hydroxyanisole, citric acid and edetate disodium and mixtures thereof.

In another aspect of this embodiment, the composition further comprises one or more components selected from the group consisting of sodium lauryl sulfate, croscarmellose sodium, povidone, microcrystalline cellulose and lactose monohydrate.

In a third embodiment of this invention there is provided an oral dosage unit comprised of from 5 mg to 20 mg, and particularly 10 mg, of ezetimibe; from 5 mg to 80 mg, and particularly a dosage amount selected from 5 mg, 10 mg, 20 mg, 40 mg and 80 mg, of simvastatin; and from 0.002 mg to 0.004 mg of BHA per mg of simvastatin. More particularly, the composition also optionally comprises from 0.0005 mg to 0.001 mg of propyl gallate per mg of simvastatin. For example, the composition can be comprised of from 0.01 mg to 16 mg, and particularly from 0.02 mg to 0.16 mg of BHA, and additionally may be comprised of from 0.001 mg to 0.05 mg, and particularly from 0.005 mg to 0.04 mg of propyl gallate. Although not required, inclusion of propyl gallate in the composition is preferred.

In one aspect of the third embodiment, the dosage unit additionally comprises from 1 mg to 640 mg, and particularly from 15 mg to 120 mg of microcrystalline cellulose; from 0.5 mg to 80 mg, and particularly from 2 mg to 16 mg of HPMC; from 0.1 mg to 32 mg, and particularly from 1.5 to 12 mg of magnesium stearate; and lactose.

As discussed above, the amount of lactose in a dosage unit is a matter of choice, and can be selected to achieve the desired total tablet weight. Generally, about 1000 mg or less of lactose per dosage unit, for example from about 25 mg to 1000 mg, may be used to produce a dosage unit of practicable size.

In another aspect of the third embodiment, croscarmellose sodium may optionally be included as a component in the composition. For example, an oral dosage unit may contain from 0 mg to 80 mg (i.e., 80 mg or less) of croscarmellose sodium, and particularly from 3 mg to 24 mg of croscarmellose sodium.

In another aspect of the third embodiment, citric acid may optionally be included as a component in the composition. For example, an oral dosage unit may contain from 0 mg to 80 mg (i.e., 80 mg or less), and particularly from 0.25 mg to 2 mg of citric acid.

Additionally, one or more of lactic acid, malic acid, succinic acid, tartaric acid and EDTA may optionally be included in the dosage unit.

In a fourth embodiment of this invention, there is provided a method of treating one or more diseases associated with a vascular condition in a patient in need of such treatment by administering to the patient a therapeutically effective amount of a pharmaceutical composition of this invention. There is also provided a method of treating one or more diseases associated with a vascular condition in a patient in need of such treatment by administering to the patient a therapeutically effective amount of a pharmaceutical composition of this invention.

In an aspect of all embodiments of this invention, the amount of ezetimibe per dosage unit is 10 mg, and the amount of simvastatin per dosage unit is selected from:
  (a) 5 mg, wherein simvastatin is from 1% to 20%, and particularly 5% by weight of the composition;
  (b) 10 mg, wherein simvastatin is from 1% to 20%, and particularly 10% by weight of the composition;
  (c) 20 mg, wherein simvastatin is from 2% to 20%, and particularly 10% by weight of the composition;
  (d) 40 mg, wherein simvastatin is from 4% to 20%, and particularly 10% by weight of the composition; and
  (e) 80 mg, wherein simvastatin is from 8% to 20%, and particularly 10% by weight of the composition.

More specifically, when the amount of simvastatin is 5% by weight of the composition, then the amount of ezetimibe is 10% by weight of the composition, and when the amount of simvastatin is 10% by weight of the composition, then the amount of ezetimibe is selected from:
  (a) 1% to 20%, and particularly 10% by weight of the composition;
  (b) 1% to 20%, and particularly 5% by weight of the composition;
  (c) 1% to 20%, and particularly 2.5% by weight of the composition; and
  (d) 1% to 20%, and particularly 1.25% by weight of the composition.

In another aspect of all embodiments of this invention, BHA and propyl gallate are included within the composition.

In still another aspect of all embodiments of this invention, ascorbic acid is absent from the composition. Particularly, ascorbic acid is absent from the composition, and tablet dosage units formed from the bulk composition do not have a film coating over the tablets.

In yet another aspect of all embodiments of this invention, pregelatinized starch is absent from the composition. Particularly, pregelatinized starch and ascorbic acid are both absent from the composition. More particularly, pregelatinized starch and ascorbic acid are both absent from the composition, and BHA and propyl gallate are both included within the composition.

An example within the scope of this invention includes a composition comprised of ezetimibe, simvastatin, BHA and propyl gallate, wherein absent from the composition are one or both of ascorbic acid and pregelatinized starch. A further example includes a tablet pharmaceutical dosage unit comprised of ezetimibe, simvastatin, BHA and propyl gallate, wherein ascorbic acid and a film coating over the tablet are both absent from the dosage unit, or more particularly wherein ascorbic acid, pregelatinized starch and a film coating over the tablet are all absent from the dosage unit.

A granulating fluid is used to agglomerate the bulk powders to improve the processing properties of the bulk material. For the instant composition, a mixture of ethanol and water is suitable to use as the granulating fluid. Varying proportions of water:ethanol can be used, for example in the range of 10:1 to 1:3 water to ethanol on a volumetric basis. Particularly, the granulating fluid is a 3:1 ratio, on a volumetric basis, of water to ethanol. The total quantity of granulating fluid added can be varied depending on the scale of the operation. A usual range for the granulating fluid as used with the instant composition is from about 15 to 30% by weight of the composition, and particularly about 25%. The granulating fluid is removed using techniques known in the art such as tray drying, fluid bed drying, microwave drying and vacuum drying prior to compression of the bulk material into tablets.

The instant pharmaceutical composition in bulk and tablet form can be prepared by the following process. The lactose, microcrystalline cellulose, simvastatin, ezetimibe, hydroxypropyl methylcellulose and croscarmellose sodium are mixed in a high shear mixer granulator to ensure uniform distribution of each component. The granulating solvent is prepared by dissolving the BHA and propyl gallate in ethanol and the citric acid is dissolved in water. The water and ethanol solutions are then mixed and sprayed onto the powder bed in the high shear mixer granulator. The resultant wet mass is then dried and screened. It is then lubricated by the addition of magnesium stearate. The final lubricated powder blend is compressed into tablets.

More specific examples of oral dosage units are as follows. The oral dosage units described in Examples 1-6 can be made from appropriately scaled bulk composition using the process described above.

EXAMPLE 1

| Component | Amount (mg) |
| --- | --- |
| Simvastatin | 5.0 |
| Ezetimibe | 10.0 |
| Microcrystalline Cellulose | 15.0 |
| Lactose | 63.23 |
| HPMC | 2.0 |
| Croscarmellose Sodium | 3.0 |
| Citric Acid | 0.25 |
| Propyl Gallate | 0.005 |
| BHA | 0.02 |
| Magnesium Stearate | 1.5 |
| Total Tablet Weight | 100.0 |

EXAMPLE 2

| Component | Amount (mg) |
|---|---|
| Simvastatin | 10.0 |
| Ezetimibe | 10.0 |
| Microcrystalline Cellulose | 15.0 |
| Lactose | 58.23 |
| HPMC | 2.0 |
| Croscarmellose Sodium | 3.0 |
| Citric Acid | 0.25 |
| Propyl Gallate | 0.005 |
| BHA | 0.02 |
| Magnesium Stearate | 1.5 |
| Total Tablet Weight | 100.0 |

EXAMPLE 3

| Component | Amount (mg) |
|---|---|
| Simvastatin | 20.0 |
| Ezetimibe | 10.0 |
| Microcrystalline Cellulose | 30.0 |
| Lactose | 126.45 |
| HPMC | 4.0 |
| Croscarmellose Sodium | 6.0 |
| Citric Acid | 0.5 |
| Propyl Gallate | 0.01 |
| BHA | 0.04 |
| Magnesium Stearate | 3.0 |
| Total Tablet Weight | 200.0 |

EXAMPLE 4

| Component | Amount (mg) |
|---|---|
| Simvastatin | 40.0 |
| Ezetimibe | 10.0 |
| Microcrystalline Cellulose | 60.0 |
| Lactose | 262.90 |
| HPMC | 8.0 |
| Croscarmellose Sodium | 12.0 |
| Citric Acid | 1.0 |
| Propyl Gallate | 0.02 |
| BHA | 0.08 |
| Magnesium Stearate | 6.0 |
| Total Tablet Weight | 400.0 |

EXAMPLE 5

| Component | Amount (mg) |
|---|---|
| Simvastatin | 80.0 |
| Ezetimibe | 10.0 |
| Microcrystalline Cellulose | 120.0 |
| Lactose | 535.84 |
| HPMC | 16.0 |
| Croscarmellose Sodium | 24.0 |
| Citric Acid | 2.0 |
| Propyl Gallate | 0.04 |
| BHA | 0.16 |
| Magnesium Stearate | 12.0 |
| Total Tablet Weight | 800.0 |

EXAMPLE 6

| Component | Amount (mg) |
|---|---|
| Simvastatin (0.025% BHA) | 10.0 |
| Ezetimibe | 10.0 |
| Microcrystalline Cellulose | 40.0 |
| Lactose | 98.98 |
| Pregelatinized Starch | 20.0 |
| Croscarmellose Sodium | 20.0 |
| Citric Acid | 0 |
| Propyl Gallate | 0 |
| BHA | 0.02 |
| Magnesium Stearate | 1.0 |
| Total Tablet Weight | 200.0 |

The oral dosage unit described in Example 7 can be prepared as described below.

EXAMPLE 7

| Component | mg/tablet |
|---|---|
| Ezetimibe Granulation: | |
| Ezetimibe | 10.0 |
| Lactose | 53.74 |
| Microcrystalline Cellulose | 20.0 |
| Croscarmellose Sodium | 8.0 |
| Povidone | 4.0 |
| BHA | 0.01 |
| Ascorbic Acid | 2.5 |
| Citric Acid | 1.25 |
| Simvastatin Granulation: | |
| Simvastatin (0.025% BHA) | 10.0 |
| Lactose | 21.87 |
| Microcrystalline Cellulose | 10.0 |
| Croscarmellose Sodium | 4.0 |
| Povidone | 2.0 |
| BHA | 0.005 |
| Ascorbic Acid | 1.25 |
| Citric Acid | 0.625 |
| Lubricant | |
| Magnesium Stearate | 0.75 |
| Total Weight | 150.0 |

Ezetimibe Granulation: BHA and citric acid in the amounts described above for the ezetimibe granulation were dissolved in a 70:30 water/alcohol mixture. Povidone (PVP) and ascorbic acid in the amounts described above for the ezetimibe granulation were dissolved in water. The ezetimibe, lactose, half of the croscarmellose sodium and half of the microcrystalline cellulose in the amounts described above for the ezetimibe granulation were mixed in a Hobart mixer. While blending, the BHA solution described above was added to the ezetimibe mixture. The resulting mixture was granulated using the povidone/ascorbic acid solution described above. The resulting wet mass was granulated as described above and then blended with the other half of the croscarmellose sodium and microcrystalline cellulose.

Simvastatin Granulation: BHA and citric acid in the amounts described above for the simvastatin granulation were dissolved in a 7:3 water/alcohol mixture. Povidone (PVP) and ascorbic acid in the amounts described above for the simvastatin granulation were dissolved in water. The simvastatin, lactose, half of the croscarmellose sodium and half of the microcrystalline cellulose in the amounts described above for the simvastatin granulation were mixed in a Hobart mixer. While blending, the BHA solution described above was added to the simvastatin mixture. The resulting mixture was granulated using the povidone/ascorbic acid solution described above. The resulting wet mass was granulated as described above and then blended with the other half of the croscarmellose sodium and microcrystalline cellulose.

Composite Granules: The ezetimibe granules and simvastatin granules were mixed together in a Turbula mixer. Magnesium stearate was mixed with the granule mixture and compressed into tablets in a manner similar to that described above.

Accordingly, in another embodiment, the present invention provides a therapeutic combination comprising (a) a first amount of from 1% to 20% by weight of at least one sterol absorption inhibitor or a pharmaceutically acceptable salt thereof or a solvate thereof and from 0.005% to 10% by weight of at least one first stabilizing agent; and (b) a second amount of from 1% to 80% by weight of at least one HMG CoA reductase inhibitor and from 0.005% to 10% by weight of at least one second stabilizing agent, wherein the first amount and the second amount together comprise a therapeutically effective amount for the treatment or prevention of atherosclerosis. The first stabilizing agent and the second stabilizing agent can be the same or chemically different and include for example the stabilizing agents listed above.

As used herein, "therapeutic combination" means the administration of two or more therapeutic agents, such as sterol absorption inhibitor(s) and HMG CoA reductase inhibitor(s), to prevent or treat atherosclerosis or any of its associated conditions, such as are discussed above. Such administration includes coadministration of these therapeutic agents in a substantially simultaneous manner, such as in a single tablet or capsule having a fixed ratio of active ingredients or in multiple, separate capsules for each therapeutic agent. Also, such administration includes use of each type of therapeutic agent in a sequential manner. In either case, the treatment using the combination therapy will provide beneficial effects in treating the atherosclerotic condition. A potential advantage of the combination therapy disclosed herein may be a reduction in the required amount of an individual therapeutic compound or the overall total amount of therapeutic compounds that are effective in treating the atherosclerotic condition. By using a combination of therapeutic agents, the side effects of the individual compounds can be reduced as compared to a monotherapy, which can improve patient compliance. Also, therapeutic agents can be selected to provide a broader range of complimentary effects or complimentary modes of action.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. It is intended, therefore, that the invention be defined by the scope of the claims that follow and that such claims be interpreted as broadly as is reasonable.

What is claimed is:

1. A pharmaceutical composition comprising:
   (a) from 1% to 20% by weight of a cholesterol absorption inhibitor;
   (b) from 1% to 80% by weight of at least one HMG-CoA reductase inhibitor;
   (c) from 0.005% to 10% by weight of ascorbic acid;
   (d) croscarmellose sodium; and
   (e) povidone.

2. The pharmaceutical composition according to claim 1, wherein the cholesterol absorption inhibitor is ezetimibe.

3. The pharmaceutical composition according to claim 1, wherein the HMG-Co-A reductase inhibitor is simvastatin or atorvastatin.

* * * * *